US011507345B1

(12) United States Patent
Pallakoff

(10) Patent No.: US 11,507,345 B1
(45) Date of Patent: Nov. 22, 2022

(54) SYSTEMS AND METHODS TO ACCEPT SPEECH INPUT AND EDIT A NOTE UPON RECEIPT OF AN INDICATION TO EDIT

(71) Applicant: Suki AI, Inc., Redwood City, CA (US)

(72) Inventor: Matt Pallakoff, Redwood City, CA (US)

(73) Assignee: SuKI AI, Inc., Redwood City, CA (US)

(*) Notice: Subject to any disclaimer, the term of this patent is extended or adjusted under 35 U.S.C. 154(b) by 0 days.

(21) Appl. No.: 17/030,011

(22) Filed: Sep. 23, 2020

(51) Int. Cl.
| G06F 3/16 | (2006.01) |
| G06F 40/166 | (2020.01) |
| G06F 3/0488 | (2022.01) |
| G10L 15/22 | (2006.01) |
| G16H 10/60 | (2018.01) |
| G06F 3/0486 | (2013.01) |
| G06F 3/04842 | (2022.01) |

(52) U.S. Cl.
CPC ............ *G06F 3/167* (2013.01); *G06F 3/0486* (2013.01); *G06F 3/0488* (2013.01); *G06F 40/166* (2020.01); *G10L 15/22* (2013.01); *G16H 10/60* (2018.01); *G06F 3/04842* (2013.01); *G10L 2015/223* (2013.01)

(58) Field of Classification Search
CPC ...... G06F 3/167; G06F 40/166; G06F 3/0488; G06F 3/0486; G06F 3/04842; G10L 15/22; G16H 10/60
See application file for complete search history.

(56) References Cited

U.S. PATENT DOCUMENTS

| 2002/0143533 | A1* | 10/2002 | Lucas ................... G06F 3/167 704/235 |
| 2003/0154085 | A1* | 8/2003 | Kelley ................ G06F 40/174 704/275 |
| 2006/0064302 | A1* | 3/2006 | Ativanichayaphong ..................... G06F 40/174 704/235 |
| 2006/0212452 | A1* | 9/2006 | Cornacchia, III .. G06F 16/3343 |
| 2007/0130134 | A1* | 6/2007 | Ramsey ............... G06F 16/951 |
| 2009/0006083 | A1* | 1/2009 | Bachand ................ G10L 15/22 704/201 |
| 2016/0274686 | A1* | 9/2016 | Alonso Ruiz ....... G06F 3/04812 |
| 2017/0046320 | A1* | 2/2017 | Reicher ................ G06F 3/0481 |
| 2017/0060531 | A1* | 3/2017 | Abbo ..................... G10L 15/26 |

* cited by examiner

*Primary Examiner* — William L Bashore
*Assistant Examiner* — Gregory A Distefano
(74) *Attorney, Agent, or Firm* — Esplin & Associates, PC

(57) ABSTRACT

Systems and methods to accept speech input and edit a note upon receipt of an indication to edit are disclosed. Exemplary implementations may: effectuate presentation of a graphical user interface that includes a note, the note including note sections, the note sections including a first note section, the individual note sections including body fields; obtain user input from the client computing platform, the user input representing an indication to edit a first body field of the first note section; obtain audio information representing sound captured by an audio section of the client computing platform, the audio information including value definition information specifying one or more values to be included in the individual body fields; perform speech recognition on the audio information to obtain a first value; and populate the first body field with the first value so that the first value is included in the first body field.

12 Claims, 7 Drawing Sheets

SYSTEMS AND METHODS TO ACCEPT SPEECH INPUT AND EDIT A NOTE UPON RECEIPT OF AN INDICATION TO EDIT

FIELD OF THE DISCLOSURE

The present disclosure is related to accepting speech input and editing a note upon receipt of an indication to edit.

BACKGROUND

Healthcare personnel (e.g., doctors, physician assistants, nurses, etc.) and other professionals may utilize speech recognition platforms to dictate and generate notes related to a patient.

SUMMARY

One aspect of the present disclosure relates to streamlining note documentation to healthcare personnel. Such streamlining may be accomplished by a system that enables a user (e.g., a clinician) to dictate notes for a patient. In particular, the user may either, via a client computing platform, screen tap a part of a clinic note, press-and-drag a part of the clinic note, and/or dictate a part of the clinic note the user desires to edit. The user may subsequently dictate information related to the patient and view the dictation presented in the clinic note format on the client computing platform. The dictation of the information related to the patient may include values for a title field of a note section, a body field of the note section, a parameter of the body field, and/or other information related to the patient. The dictation may be obtained by the system and populated in the clinic note. The user may dictate the information partially and revisit to dictate further information. The user may provide a command for the system to import the obtained and populated values included, as presented in the clinic note, into an electronic medical record (EMR) associated with the patient.

One aspect of the present disclosure relates to a system configured to accept speech input and edit a note upon receipt of an indication to edit may include one or more hardware processors, client computing platforms, and/or other components. The system may include one or more hardware processors configured by machine-readable instructions. Instruction components may include one or more of a presentation component, a user input obtainment component, a speech recognition component, a population component, and/or other instruction components.

The presentation component may be configured to effectuate presentation of a graphical user interface that includes a note. The effectuation of presentation may be via a user interface of the client computing platform. The note may include note sections. The individual note sections may include body fields. By way of non-limiting example, the note sections may include a first note section.

The user input obtainment component may be configured to obtain user input from the client computing platform. The user input may represent an indication to edit a first body field of the first note section. The user input may include a screen tap to a part of the note to edit, press-and-drag to a part of the note to edit, location information included in audio information, and/or other information.

The speech recognition component may be configured to obtain the audio information representing sound captured by an audio section of a client computing platform. Such sound may include speech from a user associated with the client computing platform. The user may include a doctor, nurse, physician, authorized medical personnel, and/or other users. The client computing platform may include the user interface, the graphical user interface, the audio section, and/or other components. The audio information may include value definition information, location information, and/or other information. The value definition information may specify one or more values to include in the individual body fields. The location information may specify where in the note or what part of the note to edit.

The speech recognition component may be further configured to perform speech recognition on the audio information to obtain one or more values for individual body fields from the value definition information. For example, speech recognition may be performed on the audio information to obtain a first value for the first body field from the value definition information included in the audio information.

The population component may be configured to populate, based on the performance of speech recognition, individual body fields with the obtained one or more values. For example, the first body field may be populated with the obtained first value based on the performance of speech recognition and the user input that indicated the first body field to edit. Thus, the first value may be included in the first body field of the of the first note section.

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect, both local and remote. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
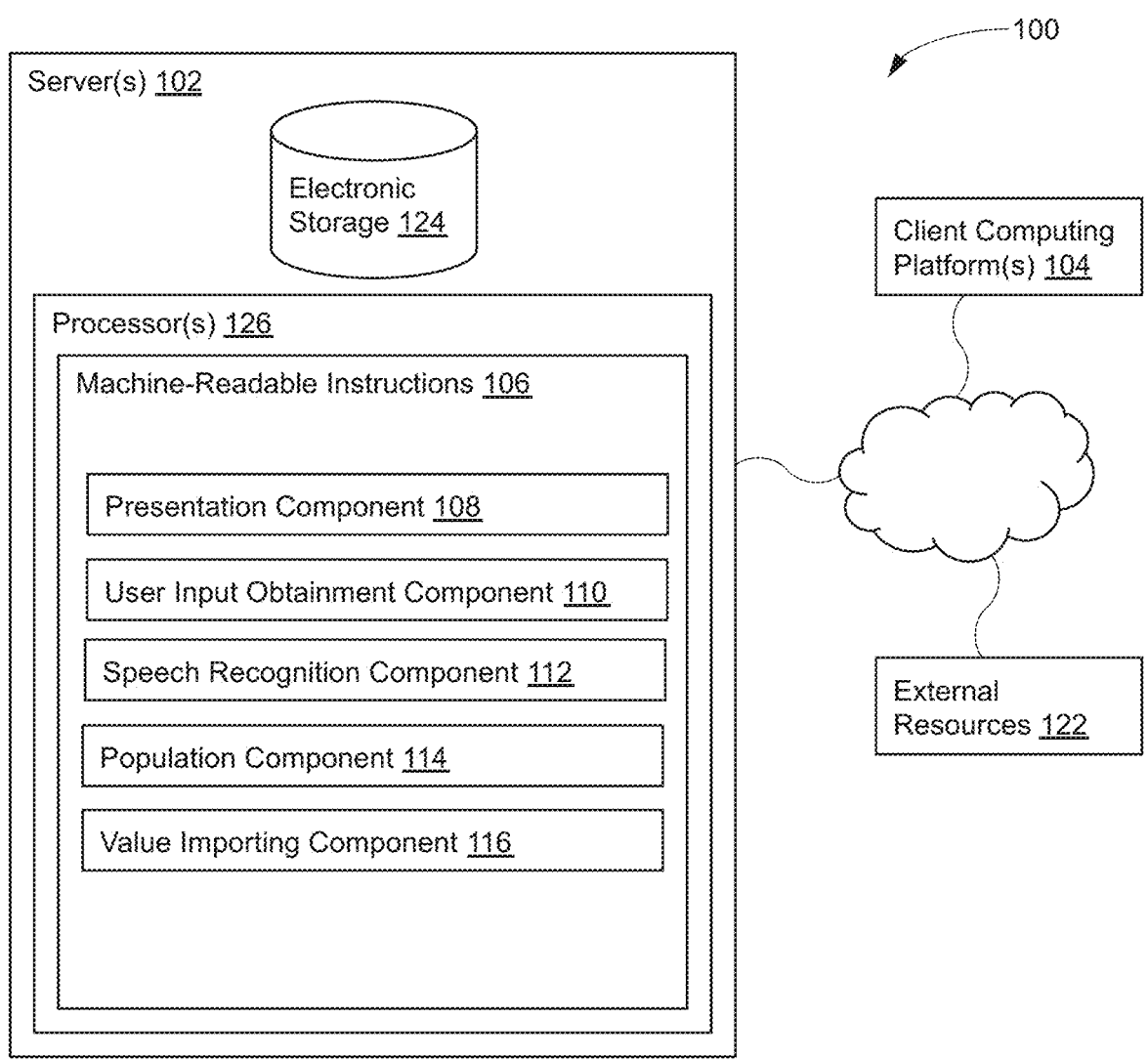
FIG. 1 illustrates a system configured to accept speech input and edit a note upon receipt of an indication to edit, in accordance with one or more implementations.

FIG. 1 illustrates a system 100 configured to accept speech input and edit a note upon receipt of an indication to edit, in accordance with one or more implementations. Editing the note may include modifying, added, and/or removing values in the note related to a patient. In some implementations, system 100 may include one or more servers 102. Server(s) 102 may be configured to communicate with one or more client computing platforms 104 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104.

Server(s) 102 may be configured by machine-readable instructions 106. Machine-readable instructions 106 may include one or more instruction components. The instruction components may include computer program components. The instruction components may include one or more of a presentation component 108, a user input obtainment component 110, a speech recognition component 112, a population component 114, a value importing component 116, and/or other instruction components.

Presentation component 108 may be configured to effectuate presentation of a graphical user interface. The graphical user interface may be a visual way of interacting with a computer using items such as windows, icons, and menus, used by most modern operating systems. The client computing platform 104 may include a user interface, a graphical user interface, an audio section, and/or other components. Presentation component 108 may be configured to effectuate presentation of the graphical user interface that includes a note. The effectuation of the presentation may be via the user interface of client computing platform 104. Individual notes may include one or more of a patient name, an age, a gender, a date of service, a medical record number, a date of birth, note sections, and/or other parts of the note that include information related to a patient. The individual note sections may include title fields, body fields, and/or other fields. The individual note sections may include information related to the patient. The individual title fields may display values of individual note sections. For example, the note sections (and corresponding title fields) may include one or more of a history of present illness, review of systems, physical exam, assessment and plan, laboratory results, prescriptions, vaccinations, patient data collected, and/or other note sections. The individual body fields may display values of individual descriptions of the note sections related to the patient and correspond to the individual title fields. In some implementations, the individual body fields may include one or more parameters and/or one or more values that correspond to the one or more parameters. In some implementations, the individual body fields may be displayed below the corresponding individual title fields, on a left side of the corresponding individual title fields, on a right side of the corresponding individual title fields, above the corresponding individual title fields, and/or other locations of the graphical user interface. By way of non-limiting example, the note sections may include a first note section. The first note section may include a first title field and a first body field. The first body field may include a first parameter, a second parameter, and/or other parameters.

By way of non-limiting example, the patient data collected may include values for blood pressure, body temperature, body weight, height, and/or other parameters for the patient data collected from the patient. The patient data collected may include patient data collected over time, day of a medical visit, over a specified period of time, and/or other time periods. The values of parameters for the patient data collected may be included in a body field for a note section (e.g., Patient Data).

User input obtainment component 110 may be configured to obtain user input from client computing platform 104. The user input may represent an indication to edit a particular note section and/or a particular part of the note. In some implementations, the user input may represent an indication to edit a title field of the particular note section. In some implementations, the user input may represent an indication to edit a body field of the particular note section. The user input that represents the indication to edit the particular note section (e.g., the body field) may include a screen tap to the corresponding body field via client computing platform 104, a screen tap to a parameter of the corresponding body field via client computing platform 104, a screen tap to an empty value corresponding to a parameter via client computing platform 104, location information, a press-and-drag to an existing value adjacent to the parameter of the corresponding body field via to the client computing platform 104, and/or other user input. The user may include a doctor, nurse, physician, authorized medical personnel, and/or other users.

The user may perform a screen tap by tapping a part of a screen of client computing platform 104 that displays a note section, title field, body field, or other part of the note the user desires to edit. The user may perform a press-and-drag by pressing and holding a part of the screen that displays a value (e.g., a value for a title field, a value for a body field, a value for a parameter, etc.), or part thereof, the user desires to edit and dragging across the value. In some implementations, the press-and-drag may be performed by pressing and holding a part of the screen where a value (e.g., a value for a parameter, a value for a title field, a value for a section field, etc.) may be presented in the note and is blank so that the user may add a value to such part of the note. Touch gestures to the part of the screen of client computing platform 104 may include a double tap, a triple tap, and/or other quantity of taps and/or combinations of screens taps and press-and-drags. In some implementations, a particular quantity or combination of the touch gestures may indicate and be associated with editing a particular portion of the note and/or particular fields of the note. For example, a triple tap on a part of the client computing platform 104 that displays a Physical Exam section may indicate a desire to edit the body field of Physical Exam as a whole and thus display indicia that the body field will be edited with the subsequent input.

Audio information may include the location information. The location information may be sound captured by an audio section and obtained by speech recognition component 112 specifying where in the note to edit. For example, the location information may specify to edit the "History of Present Illness" note section of a note.

By way of non-limiting example, the user input may represent an indication to edit the first body field of the first note section. Such user input may include one or more of a screen tap to the field body field, a screen tap to the first parameter, a screen tap to an empty value for the first parameter, the location information (included in the audio information), a press-and-drag to an existing value adjacent to the first parameter, and/or other user input.

Speech recognition component 112 may be configured to obtain the audio information representing sound captured by the audio section of the client computing platform 104. Such sound may include speech from the user associated with the client computing platform 104. The audio section may include one or more of a microphone, an audio encoder, a storage, a speaker, a processor, and/or other components. The audio information may include value definition information, the location information, and/or other information. The value definition information may specify one or more values to be included in the individual body fields, the individual title fields, the individual parameter values, and/or other parts of the note. The location information may specify where in the note or what part of the note to edit.

Speech recognition component 112 may be configured to perform speech recognition on the audio information. The performance of the speech recognition may obtain the value definition information, the location information, and/or other information. Speech recognition may be performed by various known speech recognition software. In some implementations, the performance of speech recognition on the audio information may be performed by one or more processors remote from the client computing platform 104 associated with the user. The audio information may be transmitted over a network to/from the remote one or more processors.

In some implementations, the performance of the speech recognition on the audio information may obtain one or more locations from the location information of where in the note or what part of the note to edit. By way of non-limiting example, the location obtained may be the first note section. In some implementations, the location may be the first parameter. By way of non-limiting example, a second location may be obtained. The second location may be the second parameter included in the first body field. In some implementations, upon obtaining a particular location within the note to edit, the particular location may be visually showcased. Meaning, the particular location may be more visible than other locations or parts of the note. For example, upon obtaining the location, i.e., the first note section, the first note section may be displayed in the center of the graphical user interface of client computing platform 104, displayed in its entirety, displayed brighter than other note section (or the other note section are darkened), or otherwise more visible than other parts of the note not being edited.

In some implementations, the particular location may visually display indicia to indicate where in the note will be edited with the value definition information. The indicia may include a change in background color (e.g., highlighting to be darker, highlighting to be a particular color, etc.), icons (e.g., three dots), and/or other indicia to indicate that a particular part of the note will be edited based on the user input. For example, upon the location indicating to edit a History of Present Illness note section, three dots may be displayed at a bottom of the History of Present Illness note section to indicate that such note section (i.e., body field) will be edited with the value definition information. For example, upon the second location indicating the second parameter to edit, a part of the note adjacent to the second parameter (where a corresponding value may be) may be visually highlighted a different color than a background color of the note.

In some implementations, the performance of speech recognition may obtain one or more values to populate the note with from the value definition information. In some implementations, upon performance of the speech recognition, the obtained one or more values from the value definition information may be transmitted over the network to the client computing platform 104 associated with the user. By way of non-limiting example, speech recognition component 112 may configured to perform speech recognition on the audio information to obtain a first value for the first body field from the value definition information. In some implementations, the performance of the speech recognition on the audio information may obtain a second value for the second parameter (included in the first body field) from the value definition information. The one or more values may populate a note section responsive to obtaining the one or more values and based on the user input indicating where to edit and populate the one or more values.

The audio information may be obtained by speech recognition component 112 in an ongoing manner. The term "ongoing manner" as used herein may refer to continuing to perform an action (e.g., obtaining the audio information) until receipt of an indication to terminate. The indication to terminate may include powering off client computing platform 104, charging one or more of a battery of client computing platform 104, resetting client computing platform 104, selection of a virtual button, selection of a button on client computing platform 104, and/or other indications of termination. Thus, for example, the user may speak "give the patient a shot on the right arm", subsequently provide the user input (e.g., press-and-drag) over "right arm" for user input obtainment component 110 to obtain the indication to edit "right arm", and subsequently speak "left leg" without requirement for the user to terminate and/or re-initiate the obtainment of the speech subsequent to obtainment of individual user input.

Population component 114 may be configured to populate, based on the performance of speech recognition, the note section of the note with the one or more values obtained. In some implementations, population component 114 may be configured to populate, based on the performance of speech recognition of the audio information, the body field, the title field, the one or more parameters, and/or other parts of the note with the obtained one or more values. The population of the obtained one or more values may be filling in an empty value of a particular note section, replacing an existing value of the particular note section or part thereof, adding to the value of the particular note section, and/or other populations. Where in the note to edit, or populate, may be based on the user input (e.g., the screen tap, location information included in the audio information, press-and-drag) as previously described. By way of non-limiting example, based on the performances of speech recognition, the first body field may be populated with the first value because the user input indicated the first body field to edit. As such, the first value may be included in the first body field.

In some implementations, where the user input may be the location information included in the audio information, the location obtained from the location information may be a particular note section (e.g., the first note section) to edit. Upon obtainment of the particular note section to edit, the one or more values obtained from the value definition information may be populated in a body field of the particular note section. By way of non-limiting example, the location may be the first note section (e.g., Assessment and Plan). Upon obtaining the location from the location information (included in the audio information), population component 114 may be configured to populate the first value at the location so that the first value is included in the first body field of the first note section (e.g., body field of Assessment and Plan note section). Such population may be based on obtaining the location via speech recognition component 112.

In some implementations, the location obtained from the location information may be a particular parameter included in a particular body field to edit. In some implementations, the particular body field may have already been of focus based on the user input. In other words, the particular body field of a note section may have been presently edited a moment ago, and the location obtained from the location information (e.g., "Suki, temperature") may be a parameter in that particular body field. By way of non-limiting example, the location may be the first parameter of the first body field (e.g., Temperature parameter included in a body field of Patient Data note section). The first body field may have been edited a moment ago. Upon obtaining the location (i.e., the first parameter) from the location information, population component 114 may be configured to populate the first value (e.g., 99.1 degrees) at the first parameter so that the first value is included in the first body field adjacent to the first parameter. In some implementations, population of the first value at the first parameter may include the first value in the body field so that the first parameter is replaced with the first value. Meaning, the first parameter (e.g., Temperature) may no longer be displayed, but the first value obtained (e.g., 99.1 degrees) may be populated, and thus displayed, instead.

In some implementations, the body field that includes the particular parameter to be edit, as indicated by the location information, need not be edited moments ago. Meaning, a second note section may have been edited (e.g., Physical Exam note section) moments ago, and the location information may include the second location to edit. The second location may be the second parameter. The second parameter may not be included in the second note section and may be included in the first body field of the first note section. As such, upon obtainment of the second location, population component 114 may be configured to populate the first body field with the second value at the second location so that the second value is included in the first body field adjacent to the second parameter. Such population may be based on the performance of speech recognition to obtain the second location (i.e., the second parameter) from the location information and to obtain the second value from the value definition information.

Figure 3A:
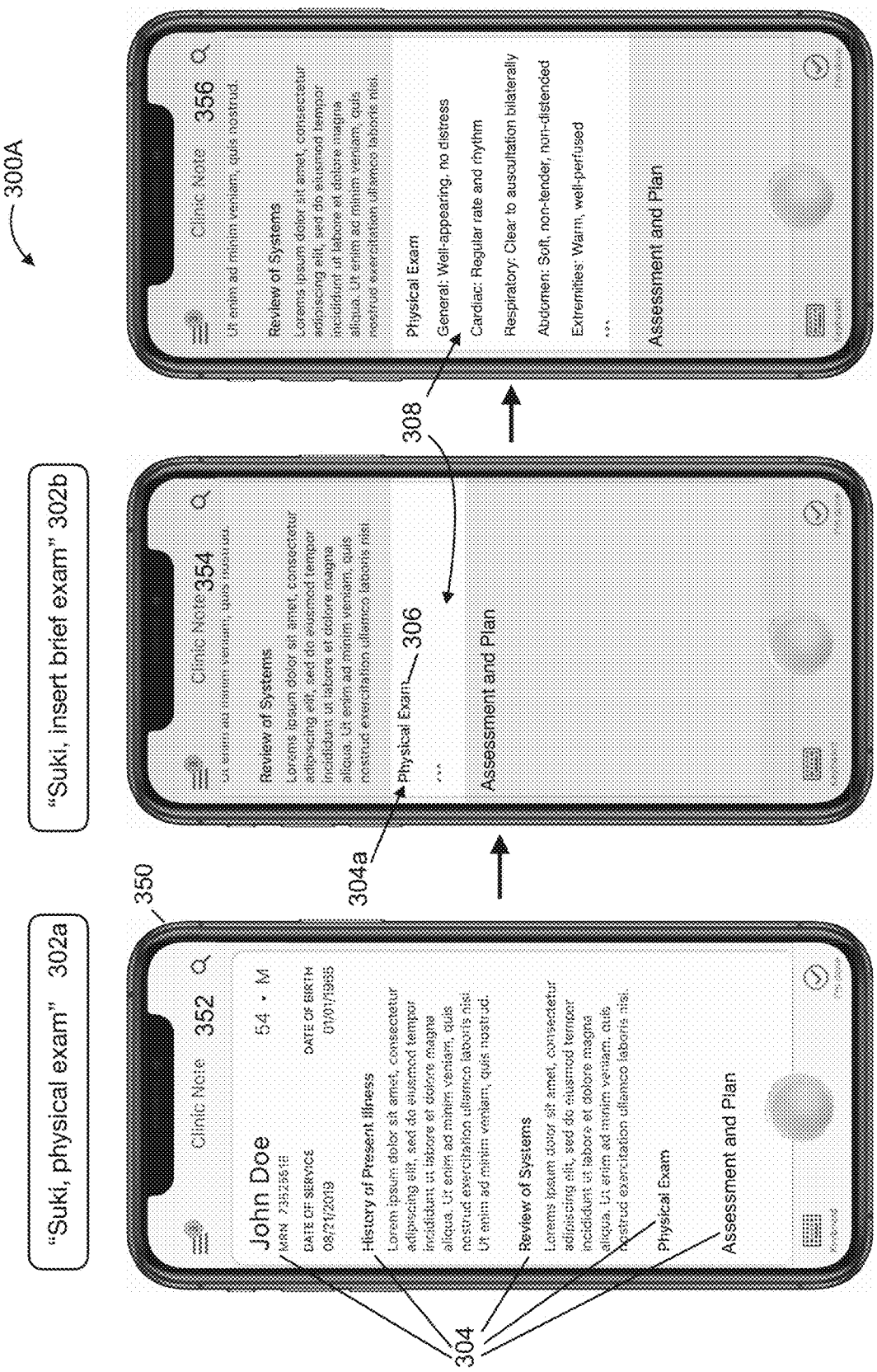
FIG. 3A-3E illustrate example implementations of a system configured to accept speech input and edit a note upon receipt of an indication to edit, in accordance with one or more implementations.

FIG. 3A-E may illustrate an example implementation of a system configured to accept speech input and edit a note upon receipt of an indication to edit, in accordance with one or more implementations. FIG. 3A may illustrate population 300A of note sections in a note 352 via a smartphone 350. Smartphone 350 may display note 352 that includes note sections 304. A doctor may dictate audio 302a. Audio 302a may include location information that corresponds to a note section the doctor desires to edit. Smartphone 350 may capture and performs speech recognition on audio 302a to obtain a location (e.g., Physical Exam) in note 352 to edit from the location information. Based on the location, note 354 (the same as note 352) showcasing a note section 304a may be displayed via smartphone 350 for editing. Note section 304a may include a title section 306 and a body field 308. The doctor may subsequently dictate audio 302b to edit body field 308 to include parameters related to a brief exam. Therefore, note 356 (the same as note 354) may be displayed where body field 308 includes parameters (e.g., General, Cardiac, Respiratory, Abdomen, Extremities) and corresponding values.

Figure 3B:
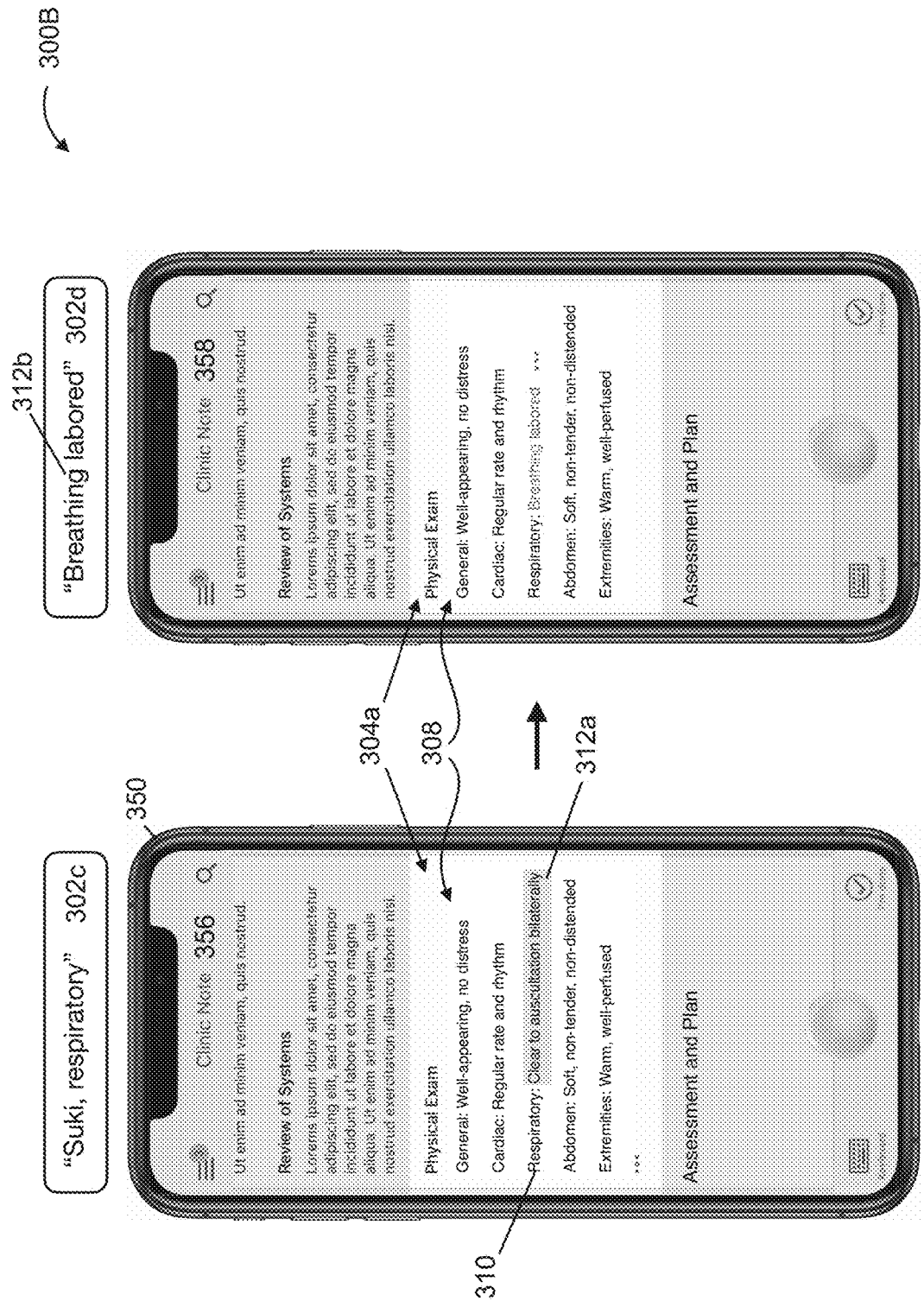

FIG. 3B may illustrate population 300B of note section 304a via smartphone 350. Smartphone 350 may display note 356 (same from FIG. 3A) that includes note section 304a. The doctor may dictate audio 302c to edit a value 312a of a parameter 310 (e.g., Respiratory) included in body field 308. Value 312a being edited may be highlighted or otherwise visually indicated as being edited. The doctor may dictate audio 302d to replace value 312a with a value 312b (e.g., breathing labored) included in and obtained from audio 302d. Thus, note 358 (the same as note 536) may display value 312b adjacent to parameter 310 instead of value 312a.

Referring back to FIG. 1, in some implementations, populating a value may include filling in an empty value for a body field and/or a parameter. For example, the second parameter included in the first body field may not have a corresponding value (i.e., an empty value). Upon a screen tap to the second parameter of the first body field via client computing platform 104, population component 114 may be configured to populate the first body field with the second value. As such, the second value may be included in the first body field adjacent to the second parameter based on the screen tap to the second parameter. In some implementations, upon a screen tap to the empty value of the second parameter via client computing platform 104, population component 114 may be configured to populate the first body field with the second value. As such, the second value may be included in the first body field adjacent to the second parameter based on the screen tap to the second parameter.

In some implementations, populating a value may be replacing an existing value of a body field and/or a parameter, or part thereof. For example, the first parameter included in the first body field may have a corresponding existing value adjacent to the first parameter. Upon the press-and-drag to the existing value included in the first body field via client computing platform 104, population component 114 may be configured to populate the first body field with the first value. As such, the first value may be included in the first body field adjacent to the first parameter and may replace the existing value adjacent to the first parameter at a location of the press-and-drag based on the press-and-drag to the first parameter. In some implementations, upon the screen tap to the first parameter via client computing platform 104, population component 114 may be configured to populate the first body field with the first value. As such, the first value may be included in the first body field adjacent to the first parameter and may replace the existing value adjacent to the first parameter based on the screen tap to the first parameter.

Figure 3C:
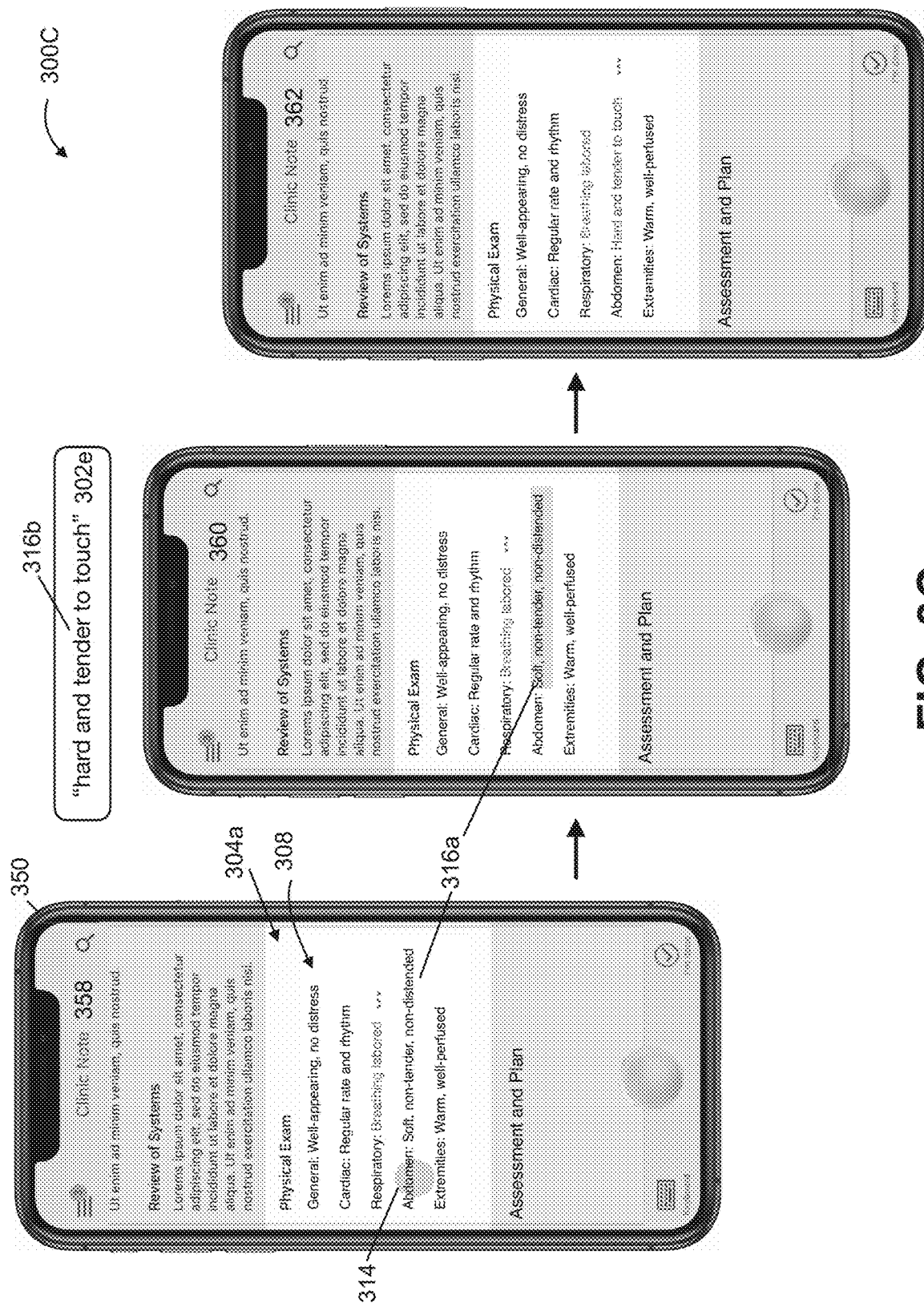

FIG. 3C may illustrate population 300C of note section 304a via smartphone 350. Smartphone 350 may display note 358 (same from FIG. 3B) that includes note section 304a. The doctor may screen tap a second parameter 314 (e.g., Abdomen) included in body field 308 as an indication to edit a value 316a that corresponds to second parameter 314. Thus, value 316a may be highlighted or otherwise visually indicated as being edited as displayed in note 360 (same as note 358). The doctor may dictate audio 302e to replace value 316a with a value 316b included in and obtained from audio 302e. Therefore, note 362 (same as note 360) may display value 316b instead of value 316a.

Figure 3D:
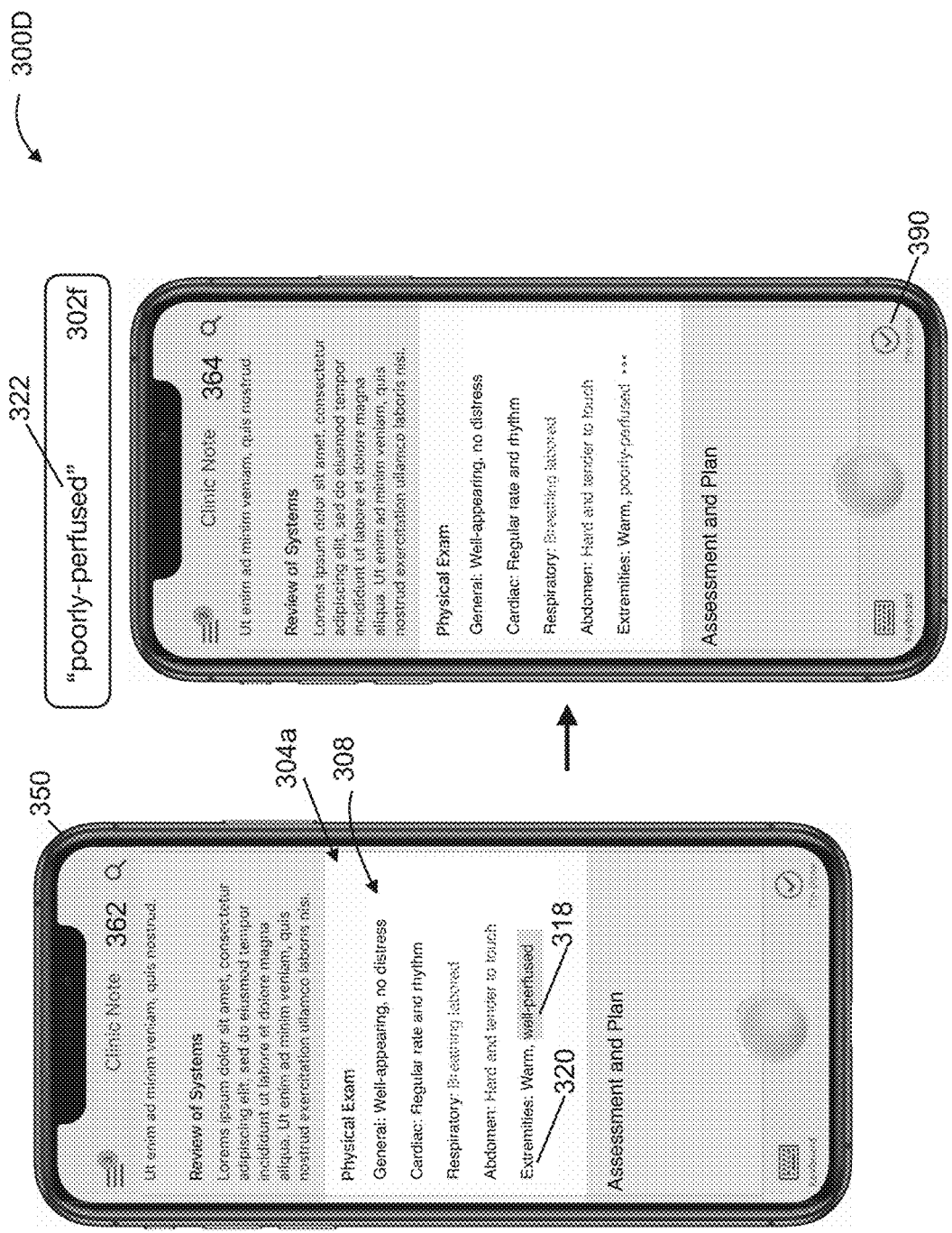

FIG. 3D may illustrate population 300D of note section 304a via smartphone 350. Smartphone 350 may display note 362 (same from FIG. 3C) that includes note section 304a. The doctor may press-and-drag across value part 318 (e.g., well-perfused) that corresponds with a parameter 320 (e.g., Extremities). The doctor may dictate audio 302f to replace value part 318 with a value 322 included in and obtained from audio 302f. Therefore, note 364 (same as note 362) may display value 322 instead of value part 318.

Figure 3E:
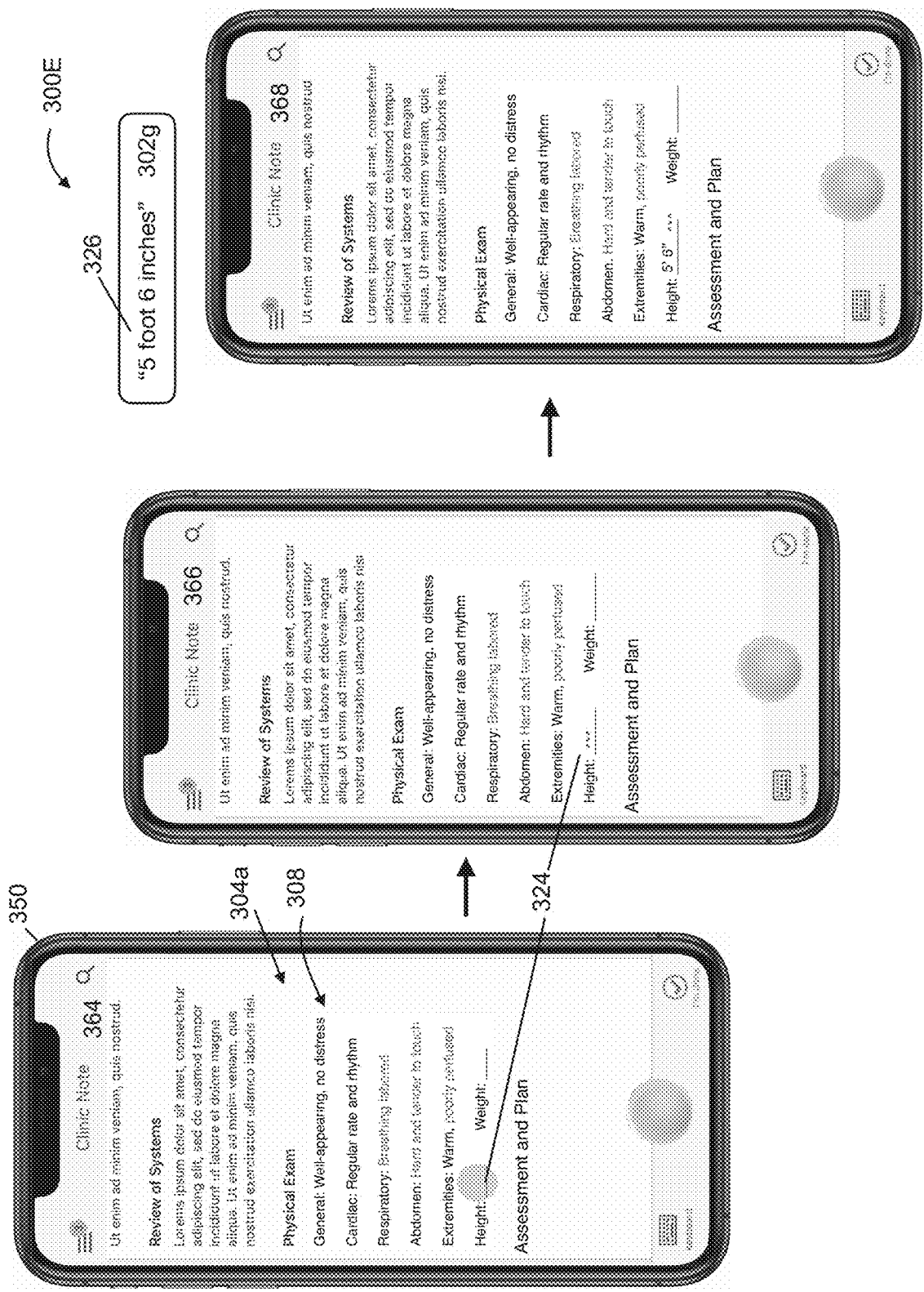

FIG. 3E may illustrate population 300E of note section 304a via smartphone 350. Smartphone 350 may display note 364 (similar to or the same as note section 364 in FIG. 3D) that includes note section 304a. Section 304a may include parameters (e.g., Height, Weight) with corresponding empty values. The doctor may screen tap an empty value 324 included in body field 308 as an indication to populate empty value 324 with value definition information. Thus, empty value 324 may be highlighted, display indicia, (e.g., three dots) or otherwise visually indicated as being edited as displayed in note 366 (same as note 364). The doctor may dictate audio 302g to populate empty value 324 with a value 326 included in and obtained from audio 302g. Therefore, note 368 (same as note 366) may display value 326, or variation thereof, (e.g., 5' 6") instead of empty value 324.

Referring back to FIG. 1, value importing component 116 may be configured to receive a command input by the user via the user interface of the client computing platform 104 to import the one or more values included in the note to an EMR associated with the patient. The command may include selection of a button, swiping (e.g., left, right, up, down), double tapping, hold-down tap, audio information representing a desire to import, and/or other commands input by the user. In some implementations, the command may be the indication to terminate obtaining the audio information in the ongoing manner. As used herein, the term "EMR" (or variations thereof) may refer to a digital database record established via a third-party electronic health record software, established local to a healthcare organization, and/or other recordation platforms so that the digital database record stores the patient data, the values included in the note, and/or other information related to a particular patient. The one or more values included in the note may include the one or more values for the body fields, parameters of the body fields, the title fields, and/or other parts of the note. In some implementations, the one or more values may be imported as presented in the individual body fields to the EMR associated with the patient. The EMR may be managed by authorized users of a healthcare organization and capable of being distributed to client computing platforms associated with authorized users of other healthcare organizations. Thus, by way of non-limiting example, value importing component 116 may be configured to receive a command input by the user via the user interface of the client computing platform to import the values of included in the individual body fields (e.g., the first body field) to the EMR associated with the patient. The values included in the individual body fields (e.g., the first body field) may be imported as presented in the individual body fields.

Value importing component 116 may be configured to, responsive to reception of the commands to import, import the one or more values included in the note to the EMR associated with the patient. For example, the one or more values included in the individual body fields may be imported to the EMR associated with the patient. The one or more values included in the individual body fields may be imported to the EMR as presented in the individual body fields. By way of non-limiting example, value importing component 116 may be configured to, responsive to reception of the command, import the one or more values included in the first body field to the EMR associated with the patient. The or more values included in the first body field may be imported as presented in the first body field.

Referring back to FIG. 3D, the doctor may select button 390 to command importing the values included in note section 304a, as presented in note section 304a of note 364 to the EMR associated with the patient.

Referring back to FIG. 1, in some implementations, server(s) 102, client computing platform(s) 104, and/or external resources 122 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 122 may be operatively linked via some other communication media.

A given client computing platform 104 may include one or more processors configured to execute computer program components. The computer program components may be configured to enable an expert or user associated with the given client computing platform 104 to interface with system 100 and/or external resources 122, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 122 may include sources of information outside of system 100, external entities participating with system 100, and/or other resources. In some implementations, some or all of the functionality attributed herein to external resources 122 may be provided by resources included in system 100.

Server(s) 102 may include electronic storage 124, one or more processors 126, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 124 may comprise non-transitory storage media that electronically stores information. The electronic storage media of electronic storage 124 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 124 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 124 may include one or more virtual storage resources (e.g., cloud storage, a virtual private network, and/or other virtual storage resources). Electronic storage 124 may store software algorithms, information determined by processor(s) 126, information received from server(s) 102, information received from client computing platform(s) 104, and/or other information that enables server(s) 102 to function as described herein.

Processor(s) 126 may be configured to provide information processing capabilities in server(s) 102. As such, processor(s) 126 may include one or more of a digital processor, an analog processor, a digital circuit designed to process information, an analog circuit designed to process information, a state machine, and/or other mechanisms for electronically processing information. Although processor(s) 126 is shown in FIG. 1 as a single entity, this is for illustrative purposes only. In some implementations, processor(s) 126 may include a plurality of processing units. These processing units may be physically located within the same device, or processor(s) 126 may represent processing functionality of a plurality of devices operating in coordination. Processor(s) 126 may be configured to execute components 108, 110, 112, 114, and/or 116, and/or other components. Processor(s) 126 may be configured to execute components 108, 110, 112, 114, and/or 116, and/or other components by software; hardware; firmware; some combination of software, hardware, and/or firmware; and/or other mechanisms for configuring processing capabilities on processor(s) 126. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, 112, 114, and/or 116 are illustrated in FIG. 1 as being implemented within a single processing unit, in implementations in which processor(s) 126 includes multiple processing units, one or more of components 108, 110, 112, 114, and/or 116 may be implemented remotely from the other components. The description of the functionality provided by the different components 108, 110, 112, 114, and/or 116 described below is for illustrative purposes, and is not intended to be limiting, as any of components 108, 110, 112, 114, and/or 116 may provide more or less functionality than is described. For example, one or more of components 108, 110, 112, 114, and/or 116 may be eliminated, and some or all of its functionality may be provided by other ones of components 108, 110, 112, 114, and/or 116. As another example, processor(s) 126 may be configured to execute one or more additional components that may perform some or all of the functionality attributed below to one of components 108, 110, 112, 114, and/or 116.

Figure 2:
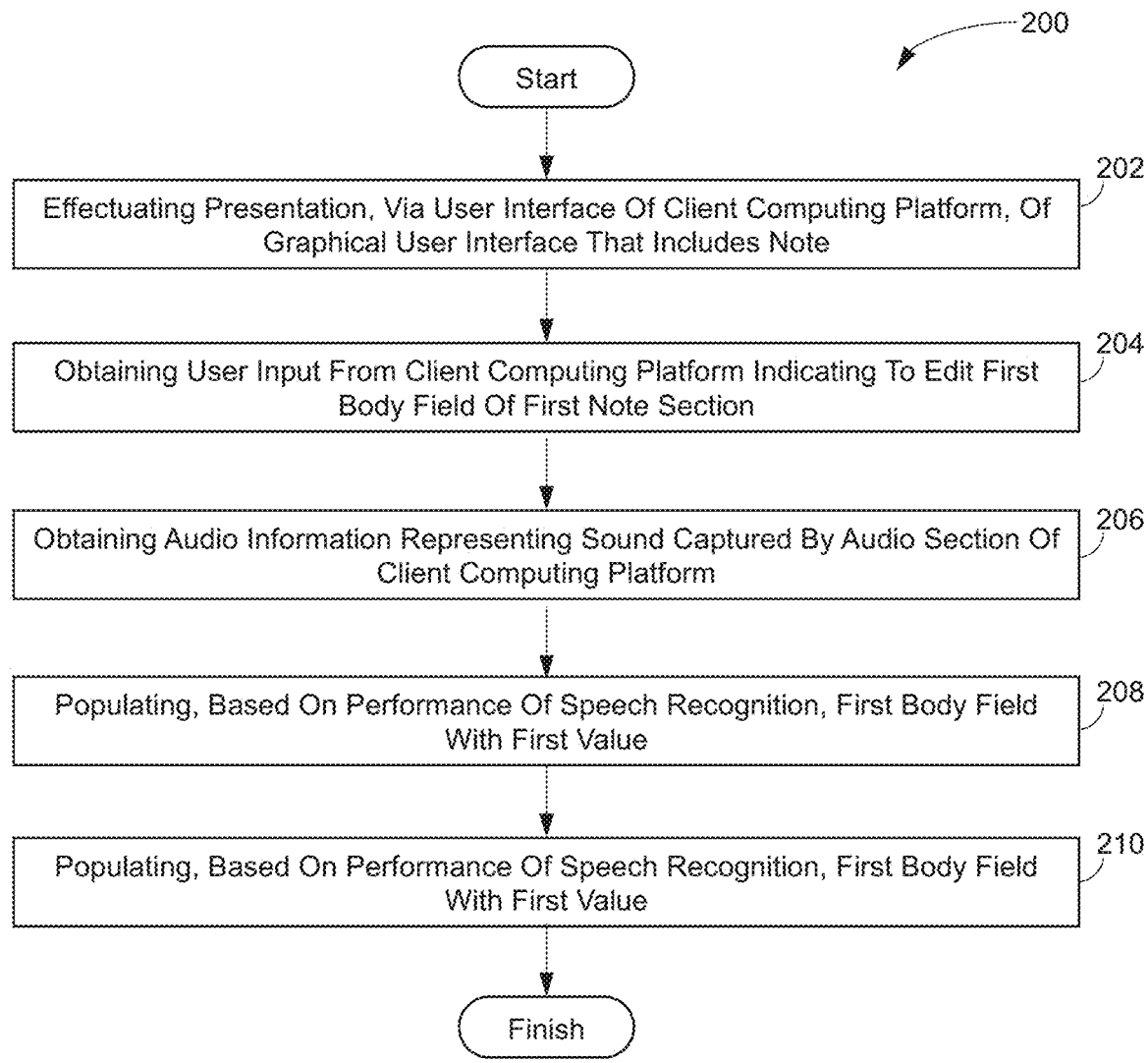
FIG. 2 illustrates a method to accept speech input and edit a note upon receipt of an indication to edit, in accordance with one or more implementations.

FIG. 2 illustrates a method 200 to accept speech input and edit a note upon receipt of an indication to edit, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include effectuating presentation, via the user interface of the client computing platform, of the graphical user interface that includes the note. The note may include the note sections. The individual note sections may include title fields and body fields. Operation 202 may be performed by one or more hardware processors configured by machine-readable instructions including a component that is the same as or similar to presentation component 108, in accordance with one or more implementations.

An operation 204 may include obtaining the user input from the client computing platform. The user input may represent an indication to edit a first body field of the first note section. The user input may include a screen tap, press-and-drag over a part of the note, location information, and/or other information. Operation 204 may be performed by one or more hardware processors configured by machine-readable instructions including a component that is the same as or similar to user input obtainment component 110, in accordance with one or more implementations.

An operation 206 may include obtaining audio information representing sound captured by the audio section of the client computing platform. Such sound may include speech from the user associated with the client computing platform. The audio information may include value definition information specifying one or more values to be included in the individual body fields. Operation 206 may be performed by one or more hardware processors configured by machine-readable instructions including a component that is the same as or similar to speech recognition component 112, in accordance with one or more implementations.

An operation 208 may include performing speech recognition on the audio information to obtain a first value for the first body field from the value definition information included in the audio information. Operation 208 may be performed by one or more hardware processors configured by machine-readable instructions including a component that is the same as or similar to speech recognition component 112, in accordance with one or more implementations.

An operation 210 may include populating, based on the performance of speech recognition, the first body field with the first value. As such, the first value may be included in the first body field. The user input may have indicated the first body field to edit. Operation 210 may be performed by one or more hardware processors configured by machine-readable instructions including a component that is the same as or similar to population component 114, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to accept speech input and edit a note upon receipt of an indication to edit, the system comprising:
    one or more processors configured by machine-readable instructions to:
        effectuate presentation, via a user interface of a client computing platform associated with a user, of a graphical user interface that includes a note, wherein the note includes note sections, the note sections including a first note section, the individual note sections including body fields;
        obtain user input from the client computing platform, wherein the user input represents an indication to edit a first body field of the first note section;

obtain audio information representing sound captured by an audio section of the client computing platform, such sound including speech from the user associated with the client computing platform, wherein the audio information includes first audio information, wherein the first audio information includes a name that corresponds to first value definition information, the first value definition information specifying a set of parameters that are related and corresponding values to be inserted in the individual body fields;

perform speech recognition on the first audio information to obtain the set of the parameters that are related and the corresponding values for inclusion in the first body field based on the name and the first value definition information included in the first audio information;

populate, based on the performance of speech recognition on the first audio information, the first body field with the set of the parameters and the corresponding values so that the set of the parameters and the corresponding values is included in the first body field;

obtain second audio information captured by the audio section, wherein the second audio information includes a first parameter and second value definition information specifying a first value to the first parameter to be included in the first body field, wherein the first parameter is one of the parameters in the set;

perform speech recognition on the second audio information to obtain the first value for the first body field from the second value definition information included in the second audio information;

populate, based on the performance of speech recognition on the second audio information, the first body field with the first value so that the first value corresponds to the first parameter, wherein the population of the first body field with the first value includes replacing one of the corresponding values with the first value; and simultaneous to the populations, effectuate presentation of the populations to the note via the graphical user interface.

2. The system of claim 1, wherein the user input that represents the indication to edit the first body field includes a screen tap to the first body field via the client computing platform, a screen tap to a first section that corresponds to the first body field via the client computing platform, location information, and/or a press-and-drag to the first body field via to the client computing platform, wherein the audio information includes the location information specifying where in the first body field to edit.

3. The system of claim 2, wherein the one or more processors are further configured by machine-readable instructions to:
perform speech recognition on the audio information to determine the first body field to edit from the location information, wherein the first body field corresponds to the first note section.

4. The system of claim 1, wherein the individual note sections include title fields.

5. The system of claim 1, wherein the first body field includes a second parameter, wherein the second audio information includes the second parameter and second value definition information such that performing the speech recognition on the second audio information include obtaining a second value for the second parameter from the second value definition information, wherein the one or more processors are further configured by machine-readable instructions to:
obtain second user input indicating to edit a value corresponding to the second parameter, wherein the second user input includes a screen tap to the second parameter via the client computing platform
and
populate, based on the performance of speech recognition on the second audio information, the first body field with the second value so that the second value is included in the first body field adjacent and corresponding to the second parameter.

6. The system of claim 1, wherein the one or more processors are further configured by machine-readable instructions to:
receive a command input by the user via the user interface of the client computing platform to import the one or more values included in the individual body fields, as presented in the individual body fields, to an electronic medical record associated with a patient; and
responsive to reception of the command, import the one or more values included in the individual body fields, as presented in the individual body fields, to the electronic medical record associated with the patient.

7. A method to accept speech input and edit a note upon receipt of an indication to edit, the method comprising:
effectuating presentation, via a user interface of a client computing platform associated with a user, of a graphical user interface that includes a note, wherein the note includes note sections, the note sections including a first note section, the individual note sections including body fields;

obtaining user input from the client computing platform, wherein the user input represents an indication to edit a first body field of the first note section;

obtaining audio information representing sound captured by an audio section of the client computing platform, such sound including speech from the user associated with the client computing platform, wherein the audio information includes first audio information, wherein first the audio information includes a name that corresponds to first value definition information, the first value definition information specifying a set of parameters that are related and corresponding values to be inserted in the individual body fields;

performing speech recognition on the first audio information to obtain the set of the parameters that are related and the corresponding values for inclusion in the first body field based on the name and the first value definition information included in the first audio information;

populating, based on the performance of speech recognition on the first audio information, the first body field with the set of the parameters and the corresponding values so that the set of the parameters and the corresponding values is included in the first body field;

obtaining second audio information captured by the audio section, wherein the second audio information includes a first parameter and second value definition information specifying a first value to the first parameter to be included in the first body field, wherein the first parameter is one of the parameters in the set;

performing speech recognition on the second audio information to obtain the first value for the first body field from the second value definition information included in the second audio information;

populating, based on the performance of speech recognition on the second audio information, the first body field with the first value so that the first value corresponds to the first parameter, wherein the population of the first body field with the first value includes replacing one of the corresponding values with the first value; and simultaneous to the populations, effectuating presentation of the populations to the note via the graphical user interface.

8. The method of claim 7, wherein the user input that represents the indication to edit the first body field includes a screen tap to the first body field via the client computing platform, a screen tap to a first section that corresponds to the first body field via the client computing platform, location information, and/or a press-and-drag to the first body field via to the client computing platform, wherein the audio information includes the location information specifying where in the first body field to edit.

9. The method of claim 8, further comprising:

performing speech recognition on the audio information to determine the first body field to edit from the location information, wherein the first body field corresponds to the first note section.

10. The method of claim 7, wherein the individual note sections include title fields.

11. The method of claim 7, wherein the first body field includes a second parameter, wherein the second audio information includes the second parameter and second value definition information such that performing the speech recognition on the second audio information include obtaining a second value for the second parameter from the second value definition information, further comprising:

obtain second user input indicating to edit a value corresponding to the second parameter, wherein the second user input includes a screen tap to the second parameter via the client computing platform populating, based on the performance of speech recognition on the second audio information, the first body field with the second value so that the second value is included in the first body field adjacent and corresponding to the second parameter.

12. The method of claim 7, further comprising:

receiving a command input by the user via the user interface of the client computing platform to import the one or more values included in the individual body fields, as presented in the individual body fields, to an electronic medical record associated with a patient; and responsive to reception of the command, importing the one or more values included in the individual body fields, as presented in the individual body fields, to the electronic medical record associated with the patient.

* * * * *